United States Patent [19]

Knoll

[11] Patent Number: 5,468,374
[45] Date of Patent: Nov. 21, 1995

[54] MINIATURIZED SENSOR COMPONENT FOR MEASURING CONCENTRATIONS OF SUBSTANCES IN LIQUIDS, AND METHOD OF MANUFACTURING SUCH A COMPONENT

[76] Inventor: Meinhard Knoll, Geschwister Scholl-Strasse 9, D-4430 Steinfurt-Burgsteinfurt, Germany

[21] Appl. No.: 90,107

[22] PCT Filed: Nov. 2, 1992

[86] PCT No.: PCT/EP92/02505

§ 371 Date: Nov. 4, 1993

§ 102(e) Date: Nov. 4, 1993

[87] PCT Pub. No.: WO93/10443

PCT Pub. Date: May 27, 1993

[30] Foreign Application Priority Data

Nov. 13, 1991 [DE] Germany ............ 41 37 261.1

[51] Int. Cl.⁶ .................. B01D 69/00; G01N 27/40
[52] U.S. Cl. .................. 210/96.2; 156/250; 204/415; 204/418; 204/419; 210/490; 427/245
[58] Field of Search .................. 204/415, 418, 204/419, 420, 403; 324/459; 427/245, 246; 210/85, 321.84, 96.2, 490, 500.25, 500.27, 500.29, 506, 510.1; 422/82.03; 435/29, 32, 288; 156/290, 292

[56] References Cited

U.S. PATENT DOCUMENTS

| | | | |
|---|---|---|---|
| 2,510,262 | 6/1950 | Sollner et al. | 204/418 |
| 3,668,101 | 6/1972 | Bergman | 204/415 |
| 4,454,007 | 6/1984 | Pace | 204/418 |
| 5,063,081 | 11/1991 | Cozzette et al. | 204/415 |
| 5,120,504 | 6/1992 | Petro-Poy et al. | 435/288 |
| 5,350,518 | 9/1994 | Hiti et al. | 210/490 |

FOREIGN PATENT DOCUMENTS 3135757   6/1991   Japan .................. 204/415

*Primary Examiner*—Joseph W. Drodge
*Attorney, Agent, or Firm*—Karl F. Milde, Jr.

[57] ABSTRACT

A miniaturized sensor component for measuring concentrations of substances in liquids comprises a support that contains cavities accommodating a membrane. The membrane is produced in situ by polymerization or by precipitation from a solution. An electric lead is either mechanically connected to or integrated into the membrane and is in contact with the membrane. The membrane support is a capillarized solid and the membrane is produced in the capillaries by impregnating the support with a liquid that subsequently either polymerizes or evaporates leaving a residue.

25 Claims, 2 Drawing Sheets

MINIATURIZED SENSOR COMPONENT FOR MEASURING CONCENTRATIONS OF SUBSTANCES IN LIQUIDS, AND METHOD OF MANUFACTURING SUCH A COMPONENT

BACKGROUND OF THE INVENTION

The present invention concerns a miniaturized sensor component for measuring concentrations of substances in liquids. The sensor component comprises a support. The support contains cavities. The cavities accommodate a membrane. The membrane is produced in situ by polymerization or by precipitation from a solution. An electric lead is either mechanically connected to or integrated into the membrane and is in contact with the membrane.

The present invention also concerns a method of manufacturing such a sensor component.

The membranes in miniaturized sensor components of the aforesaid genus are ion-selective. The sensors are employed in medicine to measure blood-electrolyte levels and in environmental engineering to determine how contaminated drinking water might be.

Manufacturing miniaturized ion-selective electrodes (ISE's) by the "wire-coating" method is known (P. Berveld, *Development and Application of Chemical Sensors in Liquids*, in *Sensors and Sensory Systems for Advanced Robots*, Berlin and Heidelberg, Springer, 1988, 403). A slender silver wire is coated with an ion-selective polymer membrane obtained from a liquid by immersing the wire in a solution for example.

Ion-selective electrodes can also be manufactured by coating a sheet of plastic instead of wire (U. Lemke & K. Cammann, *Coated Film Electrodes*, Fresenius Z. Anal. Chem. 335 [1989], 852–54). In their simplest form, these electrodes comprise an ion-selective polymer membrane over a thin layer of silver on the plastic.

Methods for producing such ion-selective polymer membranes are also known (Fluka Feinchemikalien Gmbh, Neu-Ulm sales literature, *Selectophore Ionophores for Ion-Selective Electrodes*). Such a membrane typically consists of a polyvinyl-chloride matrix containing both a softener and an electrically active substance (an ionophore) that determines what ions the membrane will allow through. The substance, dissolved in such a solvent as tetrahydrofuran, is cast into a membrane that solidifies as the solvent evaporates.

Slightly more complicated than the aforesaid sensor components are what are called thin-film electrodes (K. Cannann et al, *Chemo- und Biosensoren-Grundlagen und Anwendungen*, Z. Angew. Chem. 103 [1991], 519–541]. These components have a layer of silver chloride between the elemental silver and the ion-selective polymer membrane as well as a solidified layer of reference electrolytes. The reference electrolytes make it possible to establish a constant potential difference between the membrane and the silver.

The potential at the phase boundary between the solution being tested and the ion-selective membrane in such an electrode will vary with the ionic activity of the solution and hence with its concentration of ions. The variation can be compared with a reference electrode of constant potential.

Several ion-selective membranes can be combined on a common support to make a multiple sensor (European Patent Application No. 0,302,228 A2).

Using ion-selective electrodes to make biological sensor components is also known. An enzyme is established in the ion-selective membrane, at its surface, or in or on another membrane or layer of gel by adsorption, gel inclusion, covalent coupling, or cross-linking. Glucose oxidase for instance can be employed to manufacture potentiometric glucose sensors (F. Scheller & F. Schubert, *Biosensoren*, Berlin, Akademie-Verlag, 1989, 89 & 49–52).

The known sensor components have drawbacks. Thin-film electrodes for instance are complicated to manufacture. Coated-sheet electrodes are easier to make by casting or cementing, but each sensor component is made, and must accordingly be calibrated, separately.

SUMMARY OF THE INVENTION

The object of the present invention is accordingly to improve such sensor components for chemical and biological sensing devices to the extent that they can be manufactured simply and cost-effectively. The sensor components are by the way obtained from sheet. Their sensing capabilities are inherent in the sheet itself. The sheet is trimmed into a number of sensor components, all of them with more or less the same sensing capabilities. The calibration data can accordingly be extended from a few components to all the sensor components in the same batch.

This object is attained in accordance with the invention in a miniaturized sensor component of the aforesaid genus in that the membrane support is a capillarized solid and the membrane is produced in the capillaries by impregnating the support with a liquid that subsequently either polymerizes or evaporates leaving a residue.

The support can be supplied in a web or sheet and sliced lengthwise and crosswise or stamped out into many miniaturized sensor components. Prerequisite to this approach is the specific design of the final sensor component.

The support that is impregnated with the liquid can for example be ordinary filter paper, some other paper, or cellulose felt. The support can also be synthetic-fiber especially synthetic-filament felt. Similar properties can be attained if the support is a textile or knit. It can be a metal felt or textile. It can be an organic or inorganic foam, expanded glass or plastic for example. The membrane support accordingly constitutes a mechanically buttressing matrix that accommodates the gelled membrane in the capillaries of its capillary structure.

The membrane can be conventionally connected to a silver electrical contact for instance by providing the support, preferably before it is sliced up, with a conducting layer of the aforesaid type. A layer of silver can be sputtered on for example to produce a modified coated-sheet electrode.

Another layer, of gel for instance, can be applied in or over the sensor membrane in the capillarized solid. The gel can accommodate a biologically active material, an enzyme for example. The result will be a biological sensor.

The capillarized solid can as hereintofore described be filter paper, polyetrafluoroethane-filament sheet, knitted or woven glass fibers, wire, electrically conductive or metallized synthetic fiber, layers of expanded-plastic foam, or other layers that have capillaries. The solids must be able to accommodate the as yet unsolidified membrane material and distribute it uniformly over their surface due to inherent capillary action or interface forces. The solid should be 0.01 to 1 mm thick.

Such a capillarized solid can for example be impregnated with a solution of polyvinyl chloride of the type conventionally employed to make ion-selective membranes. The solution is applied to the solid by pouring, spraying, or immersion. The solvent will evaporate and leave an ion-selective polyvinyl-chloride membrane containing the ionophor that dictates the selectivity.

Ion-selective membranes can also be of silicone, rubber, photopolymerizing or electropolymerizing materials, gels, and other substances that solidify from a liquid phase.

One side can be coated with a thin layer of silver before or after the capillarized solid is impregnated with the membrane solution, resulting in a film-coated electrode. This can be done by vacuum sputtering, by silk screening with silver ink, by cementing to a grid of inert adhesive, or by chemical precipitation.

The term "active components", as used herein, is intended to mean biologically active material or ion-selective material.

One particularly interesting approach is to apply a solidified reference-electrolyte contact instead of a silver contact to one surface of the capillarized solid. This can be done by for instance accommodating the reference electrolyte itself in the solid in the form of a gel-like layer, one side provided with the ion-selective membrane and the other side with an electricity lead of silver chloride and silver. The reference electrolyte can for example be a solution of potassium chloride immobilized with such a high-viscosity substance as gelatin, agar-agar, or polyvinyl alcohol. Further characteristics of the invention are recited in the claims.

The particular advantage of the present invention is that the specific design of the chemical or biological sensor components that can be manufactured makes it possible to produce on a large surface with homogeneous sensing properties a large number of miniaturized sensor components, all with approximately the same sensing properties by slicing or stamping. The homogeneity of the properties of the membranes belonging to these sensor components derives from the homogeneity of the capillarized solids. How to manufacture the solids' basic materials, specifically the textiles, papers, filament felts, etc., with highly uniform properties is known.

The structure of the membrane is dictated by the dimensions, surface properties, etc. of the capillaries in the capillarized solids. Whether the measurements will be carried out in the atmosphere, in vitro, or in vivo, must also be taken into consideration.

A series of tests has demonstrated that, if the structure of the capillarized solids is homogeneous, the properties of the membrane and reference-electrolyte layers will also be uniform. The properties derive from the known capabilities of the capillarized solids and from the volume of the membranes and electrolyte or gel solutions applied thereto, which will distribute themselves uniformly throughout the supporting matrix due to capillary action and interface forces.

The manufacturing process comprising production of an extensive sheet and then slicing or stamping it up allows maintenance of the uniform electrochemical properties of the overall sensor-component structure. Levels measured with a few miniaturized sensor components can accordingly be transferred with adequate reproducibility to the other sensor components in the same batch.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
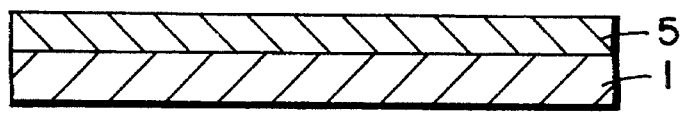
FIG. 1 is a section through part of a coated-sheet structure with a membrane and total-surface metal contact.

FIG. 1 is a schematic representation of a miniaturized sensor component comprising a membrane support 1 and a thin film 5 of silver in direct contact with the support.

Membrane support 1 is in the present case a sheet of filter paper approximately 1 mm thick, conforming to German Industrial Standard (DIN) 12448. The thickness of thin silver film 5 is drawn exaggerated. Such a film can for example be sputtered on in a vacuum or consist of tempered real-silver ink applied through a screen. Sputtered films are typically 1 µm thick and screen-printed films between 1 and 100 µm thick.

Membrane support 1 is impregnated with an appropriate membrane material, a polyvinyl-chloride solution containing a softener and an electrically active substance, an ionophore, that dictates the membrane's ionic selectivity for example. How to manufacture appropriate solutions for liquid membranes, polyvinyl-chloride or silicone-rubber membranes for example for use in ion-selective electrodes is known. The Fluka Feinchemikalien Gmbh, Neu-Ulm sales literature Selectophore Ionophores for Ion-Selective Electrodes provides examples. The solvent evaporates, leaving a membrane in situ in the membrane support's capillarized solid and secured therein. The area of the sensor component illustrated in FIG. 1 is dictated by need and purpose. A large number of miniaturized sensor components, each measuring 3×3 mm for example, are preferably sliced or stamped out of an extensive, 50×100 cm for example, web. The result is sensor components of the coated-sheet type.

When the capillarized solid is electrically conductive, it will to advantage offer less resistance in relation to its thickness than will a membrane wrapped around electrically conductive fibers since resistance depends on thickness.

Capillarized solids of this type can be made of fibers covered with a thin film of metal by sputtering or electroplating. It is alternatively also possible to use fibers that are themselves electrically conductive, consisting for instance of polyethylene thread enriched with lamp black or powdered metal.

Figure 2:
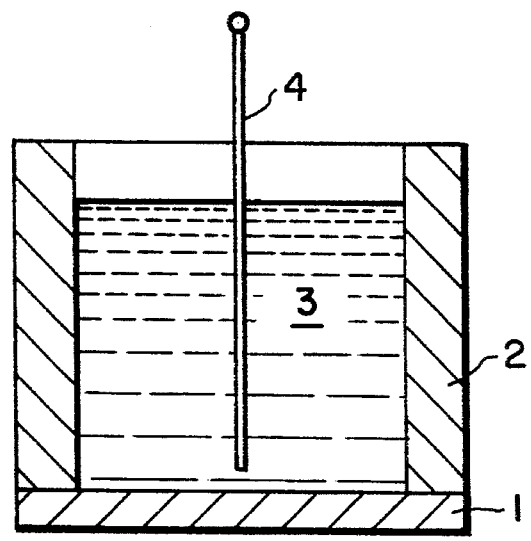
FIG. 2 illustrates an ion-selective electrode with a membrane and liquid ionic electrolyte.

FIG. 2 illustrates how a membrane support 1 impregnated with a membrane can be employed in a traditional field. The figure is a section through a conventional ion-selective electrode. The usual ion-selective polymer membrane applied to one end of a cylindrical vessel 2 is replaced by a membrane support 1 with a membrane. Cylindrical vessel 2, which may be 3 to 5 mm in diameter, is occupied by a reference-electrolyte solution 3. A silver wire 4 with a chloridized surface extends into solution 3.

The membrane support 1 in this embodiment is polyetrafluoroethane-filament gauze, a material that is in itself known. The ion-selective membrane accommodated in the support's capillaries is applied for example by pouring or spraying a polyvinyl-chloride of the aforesaid type and allowing the solvent to evaporate. The support and membrane can be cemented for instance to the end of eye 2, which is preferably plastic. A membrane support 1 manufactured in this way can accordingly be employ to advantage to construct conventional ion-selective electrodes.

Figure 3:
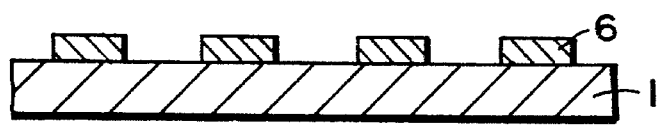
FIG. 3 is a section through part of a coated-sheet structure with separate metal contacts.

FIG. 3 illustrates another type of contact. Individual contacts 6 are employ instead of the continuous film of silver. Each contact has a diameter of 3 mm for example and are each slightly smaller than the area of miniaturized sensor component to be sliced or stamped out. These contacts can be established by sputtering through a grid or by printing with a screen The ion-selective membrane in the present case is produced in membrane support 1 for example by impregnating it with membrane liquid and polymerizing the liquid with ultraviolet light.

Figure 4:
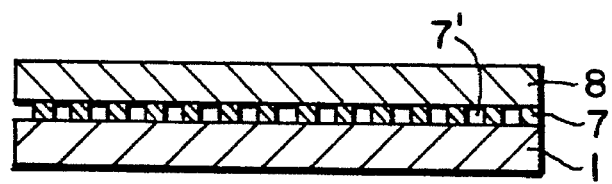
FIG. 4 is a section through part of a coated-sheet structure with cemented-on electric leads.

FIG. 4 illustrates another embodiment of a miniaturized sensor component in accordance with a modified film-coating principle. A membrane support is produced with a membrane precipitated in situ from a solution in the capillarized solid. An inert layer 7 of adhesive is now applied in the form of grid with interstices 7' that anchor a continuous film 8 of silver cemented in place over its total surface. The film contacts the membrane through interstices 7'. Another electrically conductive material can be cemented on instead of the silver. The advantage of this embodiment is that it is mechanically stable and easy to manufacture.

Figure 5:
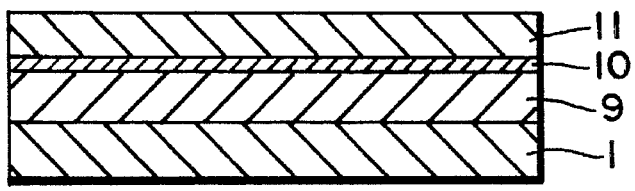
FIG. 5 is a section through part of a thin-film electrode with a membrane.

FIG. 5 illustrates a miniaturized sensor component with a reference electrolyte. A membrane support 1 and membrane are created as hereintofore described. The support can for example be plastic felt. A layer of the same material and preferably integrated into it is now provided with a solidified reference electrolyte 9. The electrolyte, potassium chloride in polyvinyl alcohol for example, can alternatively, however, be created separate and poured or sprayed on. The impregnating material will solidify into an interior reference electrolyte 9.

The surface of capillarized solid 9 is provided with a silver and silver-chloride contact before the reference electrolyte is applied. This is accomplished in the present case by sputtering a layer 10 of silver chloride on over a layer 11 of silver. Alternative approaches involve chemical precipitation or deposition of a layer of silver that is subsequently electrolytically chloridized to the interface with the supporting matrix. The matrix is for this purpose initially impregnated subsequent to the vapor deposition with silver with an appropriate chloridizing liquid that is washed out once the chloride layer has been established. If layers 1 and 9 are not identical, they can be bonded by positioning them together before the reference electrolyte is applied and securing them between two screens until the electrolyte dries or cures.

Figure 6:
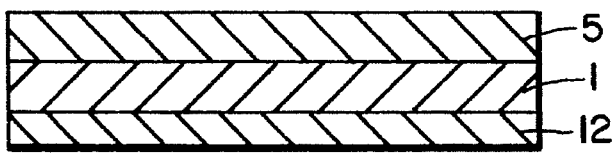
FIG. 6 illustrates a biological sensor component.

Another advantageous approach is the manufacture of what are called biological sensors. These devices are as hereintofore remarked already known. They can be produced from the miniaturized sensor component claimed herein by as illustrated in FIG. 6 providing one surface of membrane support 1, which already has a thin film 5 of silver on the other surface, with an enzyme layer 12 or with a membrane containing another biologically active material of a type appropriate for a biological sensor.

Figure 7:
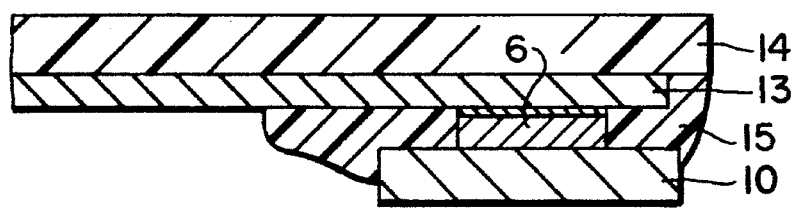
FIGS. 7 and 8 illustrate two embodiments of sensor components on supports.
Figure 8:
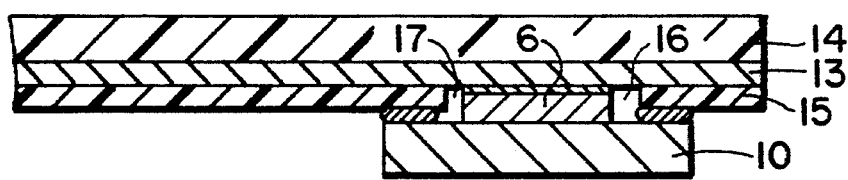

FIGS. 7 and 8, finally, illustrate various ways of applying and assembling miniaturized sensor components. An extensive membrane-supporting sheet is created impregnated with a membrane and sliced into separate chips representing miniaturized sensor components that comprise a support 10 and a contact surface 6. A sheet of the type illustrated in FIG. 3 for example can be appropriately sliced up or stamped out. Contact surface 6 is secured to a support with a plastic, polyethylene for example, tongue 14 with a layer 13 of metal on the bottom that surface 6 is cemented to with an electrically conducting silver adhesive. A miniaturized sensor component 10 is secured to the bottom of contact surface 6. To ensure that the liquid being tested penetrates between contact surface 6 and layer 13 of metal, a seal 15 of silicone resin is applied around contact surface 6 leaving the bottom of miniaturized sensor component 10 uncovered.

Support 14 can support several such layers 13 of metal and miniaturized sensor components 10 along its length or over it total area, accordingly constituting a multiple-sensor component. Such other plastics as polyetrafluoroethane or polycarbonate can alternatively be employed as support substances for plastic tongue 14.

FIG. 8 illustrates a support 14 with miniaturized sensor components 10 distributed over it that differs from the version illustrated in FIG. 7. Support 14 again has a layer 13 of metal, which is in the present embodiment, however, coated with a layer 15 of insulation. Layer 15 has an opening 17. Contact chips 6 are inserted and cemented into opening 17 with a conductive silver adhesive. A collar 16 of silicone resin 16 is cemented around the miniaturized sensor component to prevent liquid from entering the area of contact between chip 6 and layer 13 of metal.

Although the method disclosed herein is primarily intended for ion-selective electrodes, it can also be employed with other materials to obtain a desired electrochemical-sensing action. Examples of such materials are gels and liquid ion exchangers.

There has thus been shown and described a novel miniaturized sensor element for determining the concentrations of substances in liquids and process for producing the same which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In a miniaturized sensor component for measuring concentrations of substances in liquids and comprising a support that contains cavities accommodating a membrane, whereby the membrane is produced in situ by polymerization or by precipitation from a solution, an electric lead is either mechanically connected to or integrated into the membrane and is in contact with the membrane, the improvement wherein the membrane support is a capillarized solid and the membrane is produced in the capillaries by impregnating the support with a liquid, comprising membrane forming material and active components, that subsequently either polymerizes or evaporates leaving a residue.

2. Miniaturized sensor component as in claim 1, wherein the support is made of a material selected from the group consisting of filter paper, non-filter paper, and cellulose felt.

3. Miniaturized sensor component as in claim 1, wherein the support is made of synthetic fiber.

4. Miniaturized sensor component as in claim 3, wherein said synthetic fiber is synthetic-filament felt.

5. Miniaturized sensor component as in claim 1, wherein the support is a textile or knit.

6. Miniaturized sensor component as in claim 1, wherein the support is a metal felt or textile.

7. Miniaturized sensor component as in claim 1, wherein the support is an organic or inorganic foam.

8. Miniaturized sensor component as in claim 1, wherein the capillarized support is provided with a conductive layer that functions as a contact surface.

9. Miniaturized sensor component as in claim 8, wherein said conductive layer is a layer of silver.

10. Miniaturized sensor component as in claim 1, wherein the material the capillarized solid is rendered conductive by the addition of a conductive substance.

11. Miniaturized sensor component as in claim 10, wherein said conductive substance is lamp black or powdered metal.

12. Miniaturized sensor component as in claim 1, wherein the membrane support is in the form of sheet material.

13. Miniaturized sensor component as in claim 12, wherein said sheet material is an elongate web.

14. Miniaturized sensor component as in claim 1, further comprising a continuous conductive layer (5) on at least one side of the membrane support.

15. Miniaturized sensor component as in claim 1, further comprising individual contact chips (6) or surfaces on at least one side of the membrane support.

16. Miniaturized sensor component as in claim 1, for use as part of a biological-sensor component, wherein one side of the membrane support is provided with a layer (12) of enzyme or of another biologically active material.

17. Miniaturized sensor component as in claim 1, for use with a reference electrolyte, further comprising a reference in the form of a capillarized solid with an electrolyte, one side of which is bonded to a membrane support and ion-selective material and the other side of which is bonded to a silver and silver-chloride lead.

18. Miniaturized sensor component as in claim 1, wherein the miniaturized sensor component (10) is manufactured by gridlike division of a larger section of a web of impregnated membrane support.

19. Method of manufacturing support-mounted sensor components, wherein a miniature sensor component as recited in claim 18 is obtained by slicing or stamping and secured on and is in contact with a layer (13) of metal forming a contact area, subsequent to which the contact area is sealed.

20. Method as in claim 19, wherein the metal layer (13) is coated with a layer (15) of insulation that has contact-window openings (17) and in that the contact chips (6), each with a miniature sensor component (10), in positioned in them and secured in contact.

21. Method as in claim 19, wherein the miniaturized sensor component is secured with a conductive adhesive.

22. Method of as in claim 21, wherein the conductive adhesive is a conductive silver adhesive.

23. Method of manufacturing miniaturized sensor components as in claim 1, comprising providing a membrane support having a membrane which is coated with an inert layer (7) of adhesive with a grid of interstices (7') left in it and in that a continuous film of electrically conductive material is applied such that it will contact the membrane in the membrane support in the vicinity of the interstices.

24. Method of manufacturing miniaturized sensor components as in claim 23, wherein said electrically conductive material is silver.

25. Use of a miniaturized sensor component as in claim 1 as a membrane support with an ion-selective polymer membrane in an ion-selective electrode.

\* \* \* \* \*